US008852080B2

(12) United States Patent
Lewis

(10) Patent No.: US 8,852,080 B2
(45) Date of Patent: Oct. 7, 2014

(54) STIMULATION DEVICE

(76) Inventor: Adam Lewis, London (GB)

( * ) Notice: Subject to any disclaimer, the term of this patent is extended or adjusted under 35 U.S.C. 154(b) by 92 days.

(21) Appl. No.: 13/511,396

(22) PCT Filed: Nov. 30, 2010

(86) PCT No.: PCT/GB2010/051996
§ 371 (c)(1),
(2), (4) Date: Jun. 18, 2012

(87) PCT Pub. No.: WO2011/067590
PCT Pub. Date: Jun. 9, 2011

(65) Prior Publication Data

US 2013/0172669 A1 Jul. 4, 2013

(30) Foreign Application Priority Data

Dec. 4, 2009 (GB) .................................. 0921298.6

(51) Int. Cl.

| | |
|---|---|
| ***A61F 5/00*** | (2006.01) |
| ***A61H 19/00*** | (2006.01) |
| ***A61H 23/02*** | (2006.01) |
| ***A61H 1/00*** | (2006.01) |

(52) U.S. Cl.
CPC ............ *A61H 1/00* (2013.01); *A61H 2205/087* (2013.01); *A61H 19/32* (2013.01); *A61H 19/30* (2013.01); *A61H 2201/1645* (2013.01); *A61H 23/0254* (2013.01); *A61H 2201/165* (2013.01)
USPC ............................................................ 600/38

(58) Field of Classification Search
USPC .................................. 600/38–41; 601/46, 84
See application file for complete search history.

(56) References Cited

U.S. PATENT DOCUMENTS

| | | |
|---|---|---|
| 3,900,023 A | 8/1975 | McBride |
| 6,338,721 B1 | 1/2002 | Lebecque |
| 2010/0069708 A1 | 3/2010 | Tajkarimi |

FOREIGN PATENT DOCUMENTS

| | | |
|---|---|---|
| DE | 202004011565 U1 | 12/2004 |
| WO | WO-01/34028 A1 | 5/2001 |

*Primary Examiner* — John Lacyk
(74) *Attorney, Agent, or Firm* — Barnes & Thornburg LLP

(57) ABSTRACT

The invention relates to a simple and easy to use stimulatory device which allows the user to apply vibrations to the frenulum, while being an essentially hands-free device, so that the user does not have to manually hold or manipulate the device during use. In an embodiment, the device allows the user to control the amplitude and frequency of the vibrations applied to the frenulum.

10 Claims, 3 Drawing Sheets

STIMULATION DEVICE

The present invention relates to a device for controlled stimulation of the penis. More specifically, the invention relates to a light-weight and hands-free device which delivers vibrations to the frenulum. In an embodiment, the device delivers variable vibrations to the frenulum.

There are a wide variety of devices which are already available which seek to stimulate the male genitalia through a variety of means, either for medical purposes, such as sperm collection or to assist those suffering from erectile dysfunction, or simply for pleasure.

A large range of recreational products has been developed and marketed, which are commonly referred to as sex-toys. These devices seek to stimulate the male genitalia in order to give pleasure. In these circumstances, an important aim of the devices is stimulation and arousal. Often postponing the orgasm is desirable. Various different means of stimulation have been proposed in the past, offering the man varying degrees of control and requiring different levels of intervention and action by the man.

The male sex toy market is extensive but lacks variety. Despite the fact that it is known that vibration applied to the penis can cause arousal and result in orgasm and ejaculation, there are relatively few products which are actually designed to stimulate the penis through vibrations. The majority of male sex toys are ‘sleeves’ which fit over the penis and are moved by hand.

Some products do work by applying vibration, but these are either not adjustable or they fail to offer the optimum amplitude of vibrations, focusing instead on frequency. What is more, the vibrations delivered are often too low in amplitude to be effective for many men. Those devices which do aim to deliver a higher intensity of vibration are not hands free but must be manually held in place by the user Products designed to be hands-free do not offer optimum vibratory amplitude and are not adjustable. They are also designed to fit around the base of the penis. Vibrating cock rings are invariably designed to fit around the base of the penis and are not adjustable.

Products designed to be hands-free do not offer optimum vibratory amplitude and are not adjustable. They are also designed to fit around the base of the penis. Vibrating cock rings are also invariably designed to fit around the base of the penis.

Medical research has identified the required vibratory amplitude and frequency for stimulating the penis. The study reported by N. L. Brackett in Human Reproduction Update (1999) Vol. 5, No. 5, p 551-552 discusses the use of different amplitudes and frequencies of vibration in order to produce ejaculation in patients with spinal cord injury. The results suggested that vibration having a frequency of about 100 Hz and an amplitude of about 2.5 mm is suitable for causing ejaculation in patients with spinal cord injuries. This is useful in a medical setting, such as the study in question, but does not necessarily represent an optimum result for a device which is designed for recreational use.

SUMMARY OF THE INVENTION

According to a first aspect of the present invention, a device for stimulating the frenulum of the male genitalia is provided which comprises a vibratory part configured to be positioned against and apply vibrations to the frenulum and an attachment means configured to hold the vibratory part in place against the frenulum.

The invention, thus, can provide a device with the following key attributes:

1. It is hands-free;
2. It can be used when the penis is still flaccid;
3. It is designed to stimulate the frenulum.

The frenulum is the most sensitive area of the penis and it has been found that vibrations applied to this small area of the penis are very effective in causing arousal and orgasm.

In an embodiment, the device further comprises control means configured to control and/or adjust the amplitude and frequency of the vibrations applied to the frenulum.

In another embodiment, the attachment means comprises an adjustable strap.

In another embodiment, the vibratory part comprises a vibratory surface which is configured to be positioned against the frenulum. The vibratory surface may be concave and shaped to receive the penis. The vibratory surface may be a hard, flat, raised surface designed to cover the frenulum and the surrounding area. The vibratory surface may be made from a malleable material which transmits vibrations and whose shape can be moulded.

In an embodiment, the vibratory part comprises a motor having an eccentric weight mounted to a rotatable shaft.

The vibratory part can comprise a rocking beam pivotally mounted on a pivot and driven to reciprocally rock in a see-saw motion about the pivot, to thereby provide the vibrations. The pivot can be mounted such that its axis of engagement with the rocking beam can be adjusted lengthwise along the rocking beam. The pivot can comprise a pin, and the pin can extend into a slot formed lengthwise in the rocking beam and can be mounted so that its location along the slot can be adjusted. The pivot pin can be fixed in a carrier that is slidably mounted within the vibratory part of the device and held in place by an adjustment knob fixed in screw threaded engagement with the vibratory part, the arrangement being such that turning the adjustment knob causes it to screw into or out of the vibratory part and thereby move the carrier and pivot pin along the slot and relative to the rocking beam. Adjusting the location of the pivot or pivot pin allows the amplitude of the vibrations to be adjusted. The rocking beam can be driven by a connecting rod, itself driven by an eccentric drive pin on located on a rotatable drive shaft. The frequency of the vibrations imparted by the pad can be adjusted by increasing or decreasing the rotational speed of the motor.

The motor can be controlled by a control means, optionally allowing the user to adjust the frequency and/or the amplitude of the vibrations produced.

In an embodiment, the frequency of the vibrations is up to 150 Hz, more preferably up to 110 Hz. In an embodiment, the amplitude of the vibrations is up to 3 mm, more preferably up to 2.5 mm.

In a further embodiment, the control means comprises a control panel configured to control the frequency and/or amplitude of the vibrations. The control panel may be separate from the vibratory part.

In an embodiment, the control means comprises an adjustment knob configured to control the frequency and/or amplitude of the vibrations. The adjustment knob may be comprised in the vibratory part.

In another embodiment, the device is battery operated. The battery is preferably located remotely from the vibratory part, so as to minimise the size and mass of the latter and thereby enhance its hands-free capability. The battery is preferably located within a housing which is separate from the vibratory part. The battery housing can carry a control panel and/or a power switch, and can be linked to the vibratory part by a cable for supplying power from the battery to the vibratory part.

In embodiments, therefore, the invention can provide a device with the following key attributes:

1. It offers adjustable amplitude and frequency of vibration, with adjustment possible during use;
2. It is battery powered, so cheap to maintain;
3. It is compact and lightweight so easily transported.

Evidence suggests that the optimum amplitude and frequency of vibration for the purpose of pleasure varies from person to person and may also vary during use of the device. In embodiments, therefore, the invention can provide a device which is easy to use, but which allows extensive control and adjustment by the user, in order to allow the experience to be controlled.

In a second aspect of the invention, a method is provided for stimulating the frenulum of the male genitalia for pleasure, the method comprising using a device according to the first aspect of the invention or any of its embodiments.

DETAILED DESCRIPTION

Figure 1:
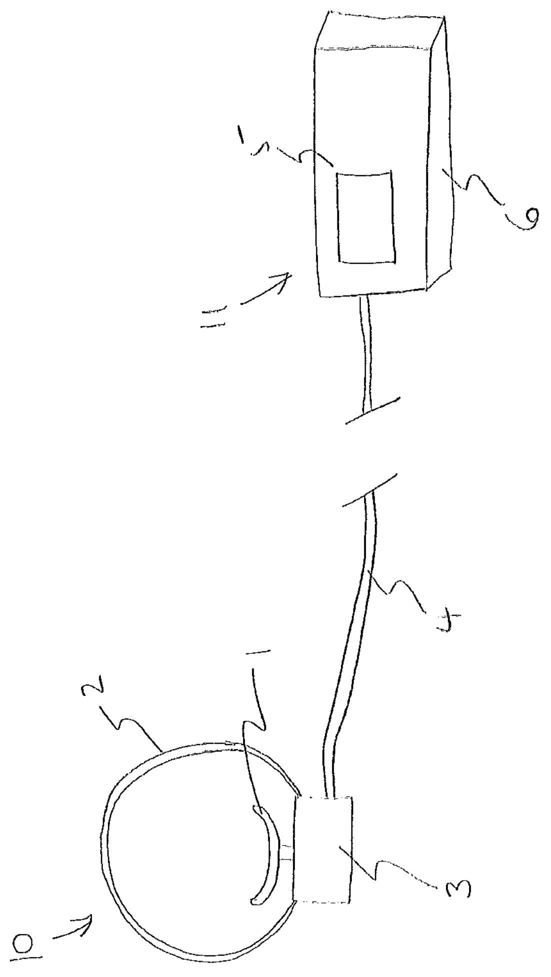
FIG. 1 is a schematic drawing of a device according to the present invention. The drawing is not to scale.

The present invention relates to a simple and easy to use stimulatory device which allows the user to apply vibrations to the frenulum of the male genitalia, whilst being an essentially hands-free device, so that the user does not have to manually hold or manipulate the device during use.

In an embodiment, the device allows the user to control the amplitude and frequency of the vibrations applied to the frenulum. Thus, in an embodiment, the invention provides a device comprising a vibratory means, or part, which applies vibrations of a controllable and adjustable amplitude and frequency to the frenulum of the male genitalia, the vibratory means, or part, being hands-free. The vibratory means, or part, can be held in place against the frenulum during use by an adjustable strap. The vibratory means, or part, can comprise a motor and a vibratory surface which contacts the frenulum.

In one embodiment of the invention, the device, and preferably the vibratory means or part of the device, can be provided with a vibrating or vibratory surface, which transmits, or is configured to transmit, the vibrations produced by the device to the frenulum. The surface may be a flat surface or it can be concave, to receive the shape of the penis and sit comfortably against the frenulum during use. Where the vibrating or vibratory surface is concave, this can also help to minimise movement of the vibrating surface relative to the frenulum during use. This is also true of alternative embodiments in which the vibrating surface is in the form of a raised platform.

The vibrating or vibratory surface is preferably formed from a material which has one or more of the following properties, and most preferably all of them: easy to clean; hypoallergenic; not heat conducting.

In one embodiment, the vibrating or vibratory surface will be a plastic material. In an alternative embodiment, the vibrating or vibratory surface may be made from a more malleable or pliable material, such as a soft rubber or gel, which transmits vibrations but which is also soft and may shape itself, to an extent, to the shape of the surface of the penis. Suitable materials will be well-known to a skilled person.

The device of the present invention is intended to be a hands-free device and to be easy and comfortable to use. As the device is attached to the penis during use, the size and weight of the part of the device, i.e., the vibratory part, which is held against the frenulum should be as small as possible. Ideally, the vibrating or vibratory surface is larger than the area of the frenulum. The vibrating or vibratory surface should not be so small that any small movement during use could render it less effective due to poor positioning.

A "hands-free" device can be a device that does not need to be manually held in place or manipulated by the user during operation. A "hands-free" device in accordance with the present invention, therefore, can comprise an attachment or holding means configured to hold the vibratory part in place against the frenulum without manual assistance after installation. The attachment means is capable of holding the vibratory part against the frenulum, without manual assistance from the user, once the device has been placed in position. The attachment means thus advantageously allows minimal intervention and action by the man during use. Devices in accordance with the invention can carry controls that can be manipulated during use. However, such embodiments are still hands free, in the sense that, once installed and running, they need no further manipulation, although the option to make adjustments remains open.

Thus, the vibrating or vibratory surface is held in place against the frenulum by the attachment or holding means. The attachment or holding means is preferably one or more adjustable straps. The straps are preferably elasticated and may be fitted when the penis is flaccid. The straps should extend sufficiently to maintain the position of the vibrating or vibratory surface with increasing tumescence of the penis. The straps may be provided with a coating which makes them relatively non-slip, to prevent movement of the vibrating surface relative to the frenulum during use.

The use of an elasticated strap has the advantage that it will become tighter as the user's erection progresses, thereby pushing the vibrating surface on to the frenulum with increasing force. This can improve the effect of the vibration.

Thus, in an embodiment, the invention provides a device comprising a vibratory means which applies vibrations of a controllable and adjustable amplitude and frequency to the frenulum of the male genitalia, the vibratory means being hands-free, wherein the vibratory means is held in place against the frenulum during use by an adjustable strap.

In alternative embodiments, the attachment or holding means may be one or more adhesive patches which are adhered to the penis and hold the vibrating or vibratory surface in place. A further alternative is a sleeve or tube which fits over at least the tip of the penis and positions the vibrating or vibratory surface adjacent the frenulum.

The attachment device may be formed from a harder material such as plastic, and may be attached to, or part of, the vibrating device. It may be held in place via a buckle, button or popper device, or it may adhere to itself.

When a strap is employed, it may be adjustable, or alternatively, straps of different sizes may be supplied.

The vibration is produced (driven) by a motor. Thus, in one embodiment, a device is provided comprising a vibratory means which applies vibrations of a controllable and adjustable amplitude and frequency to the frenulum of the male genitalia, the vibratory means being hands-free, wherein the vibratory means comprises a motor and a vibratory surface which contacts the frenulum.

The motor is preferably a small and light motor capable of producing vibrations of variable frequency and amplitude. The frequency of vibration produced is preferably up to 150 Hz, more preferably up to 110 Hz. The amplitude of the vibrations produced is preferably up to 3 mm, more preferably up to 2.5 mm. It is important to note that the frequency and amplitude of the vibrations may be adjusted constantly during use, without the need to stop or switch off the device.

In an embodiment, the vibratory part of the device comprises an electric motor with a drive pin eccentrically mounted on its output shaft. The drive pin engages a connecting rod, which extends between the drive pin and a first end portion of a rocking beam, to drive the connecting rod in lengthwise reciprocation in response to rotation of the motor's output shaft. The rocking beam has a lengthwise extending slot midway between its coupling with the connecting rod and a pad, located at the other end of the rocking beam. A pivot pin extends through the slot, and the rocking beam is arranged to "see-saw" about the pivot pin in response to lengthwise reciprocation of the connecting rod. The pad is located within the device casing such that its reciprocation, caused by the see-sawing of the rocking beam, is transmitted to the user, via a compliant portion of the casing, as vibrations. The pivot pin is mounted so that its location along the slot can be adjusted, relative to the rocking beam. Movement of the pivot pin along the slot changes the relative separation of the connecting rod, pivot pin and pad and thus provides a means for adjusting the amplitude of the vibrations the pad imparts to the user. The pivot pin is fixed in a carrier that is slidably mounted and held in place within the casing by an adjustment knob. The adjustment knob extends through and is in screw threaded engagement with the casing wall. Turning the adjustment knob causes it to screw into or out of the casing and thereby move the carrier and pivot pin along the slot and relative to the rocking beam. The frequency of the vibrations imparted by the pad can be adjusted by increasing or decreasing the rotational speed of the motor.

The motor can be controlled by a control means, optionally allowing the user to adjust the frequency and/or the amplitude of the vibrations produced.

In one embodiment, the frequency and/or amplitude of the vibrations is controlled by a control panel or unit. The frequency of the vibrations can be controlled by a button, knob or dial, on the control panel or unit. Preferably, the control panel is separate from the motor and can be easily accessed and used whilst the vibrating or vibratory surface is in position for use. Thus, in an embodiment, the control panel is separate from the vibratory means. In a preferred embodiment, the control panel is attached to the motor by a wire or cable which allows the control panel to be conveniently located during use of the device. In an alternative embodiment, the control panel may be totally detached from the motor, providing "remote control" of the device.

In an embodiment, the motor is controlled by an adjustment knob, configured to control the frequency and/or amplitude of the vibrations, and conveniently located in or on the device. The adjustment knob may be comprised in the vibratory part. For example, the adjustment knob may be located at the front end face of the vibratory part when in use, so allowing the user to easily adjust the frequency and/or the amplitude of the vibrations produced during use. Preferably, when located on the vibratory part, the adjustment knob is arranged to allow the amplitude of the vibrations to be adjusted, and the frequency of the vibrations can be adjusted via a control located remotely from the vibratory part. The frequency control can be located, preferably within a control panel, on a housing for a battery or other power supply that provides power for the device and is separate from the vibratory part of the device.

The device of the invention is preferably battery operated, although it could be mains powered. The battery is preferably located away or removed from vibratory part, including the motor and the vibrating or vibratory surface, so as to minimise the size and weight of the part of the device to be attached to the penis. In one embodiment, the battery is connected to the motor by a wire or cable, optionally like the control panel. The battery can be housed within a remote unit or housing that also carries the control panel and/or a power switch.

It would be particularly convenient for the battery to be a rechargeable battery, with the device having a charger or a charging station to allow it to be charged between uses.

For a fuller understanding of the invention, reference is now made to the accompanying drawings, which are intended to illustrate examples of possible embodiments of the invention described and claimed herein and are not intended to be limiting.

The device shown in FIG. 1 is made up of a vibrating or vibratory part 10 which is to be attached to the penis during use, and a control part 11 which is made up of the control panel and a housing 6 which houses the battery or batteries.

The vibrating or vibratory part 10 comprises a vibratory surface 1, which is held in place by an attachment or holding means, the adjustable elasticated strap 2. The vibration is produced (driven) by a small, light motor 3 which is connected by a wire 4 to the power supply (not shown) and control panel 5 which make up the control part 11 of the device.

In use, the vibrating or vibratory part 10 of the device is attached to the penis (which may be flaccid or erect), using the adjustable strap 2. The device is positioned so that the vibrating or vibratory surface 1 is against the frenulum and the strap is adjusted so that the device is held in place and is comfortable for the user. The concave shape of the vibrating or vibratory surface makes the correct positioning easier, as it is designed to complement the shape of the penis. The concave shape can also assist in keeping the part in position during use, as the shape will limit relative movement between the vibrating surface and the penis.

Once the vibrating part has been attached, the user may either hold the control part of the device or position it for easy access if required. The device may be switched on and the amplitude and frequency can be adjusted to offer a personalized and varied experience.

Figure 2:
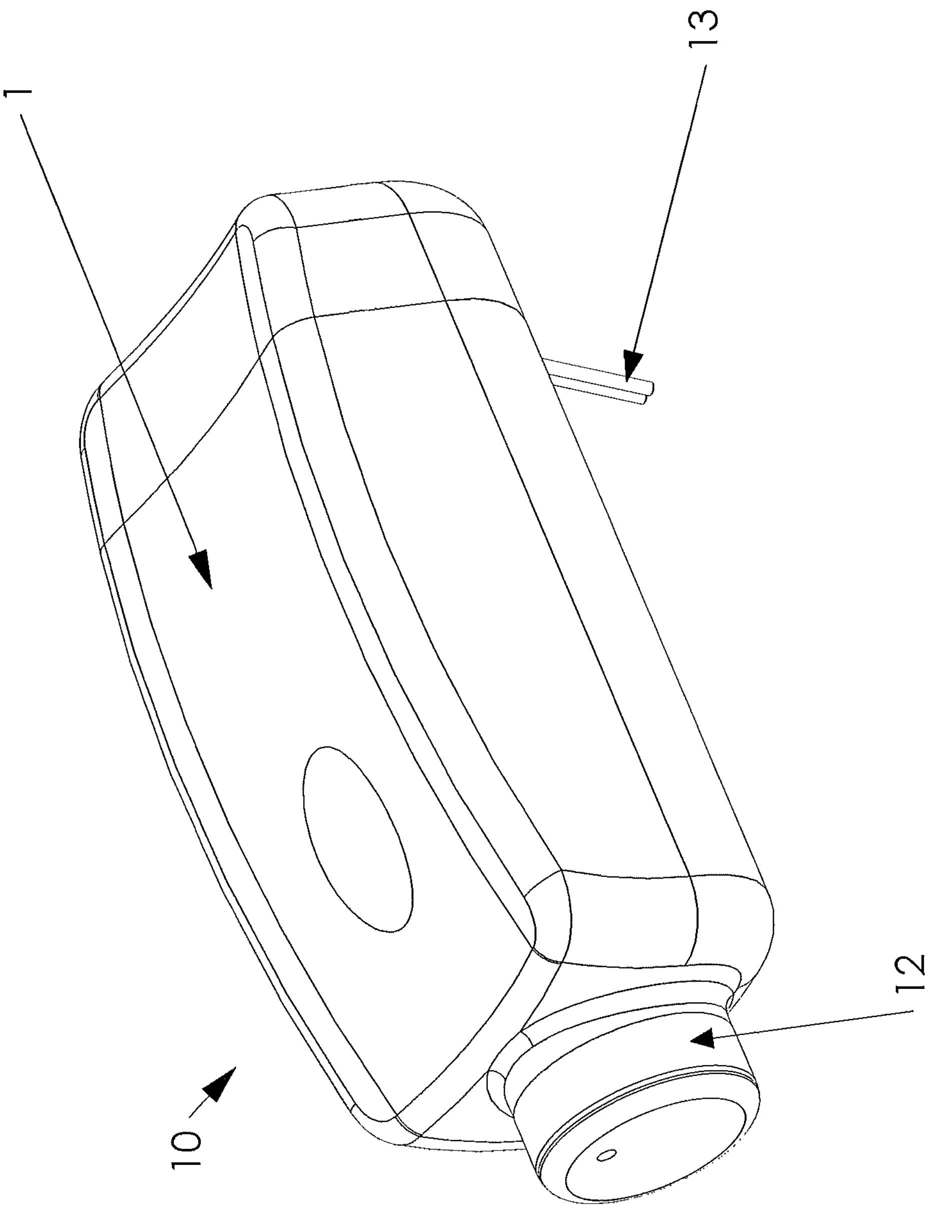
FIG. 2 is a schematic drawing of a device according to a preferred embodiment of the present invention. The drawing is not to scale.

The device shown in FIG. 2 is made up of a vibratory part 10 which is to be attached to the penis during use, featuring an adjustment knob 12.

The vibratory part 10 comprises a vibratory surface 1, which is held in place by an attachment means, such as an adjustable elasticated strap (not shown). The vibration is driven by a small, light motor, housed inside the vibratory part 10, which is connected by a wire 13 to a power supply (not shown).

In use, the vibratory part 10 of the device is attached to the penis (which may be flaccid or erect), using the attachment means. The device is positioned so that the vibratory surface 1 is against the frenulum and the attachment means is adjusted so that the device is held in place and is comfortable for the user. The concave shape of the vibratory surface makes the correct positioning easier, as it is designed to complement the shape of the penis. The concave shape can also assist in keeping the vibratory part 10 in position during use, as the shape will limit relative movement between the vibrating surface and the penis.

Once the vibratory part 10 has been attached, the device may be switched on and the amplitude and frequency can be adjusted via the adjustment knob, or a remotely located control panel, to offer a personalized and varied experience.

Figure 3:
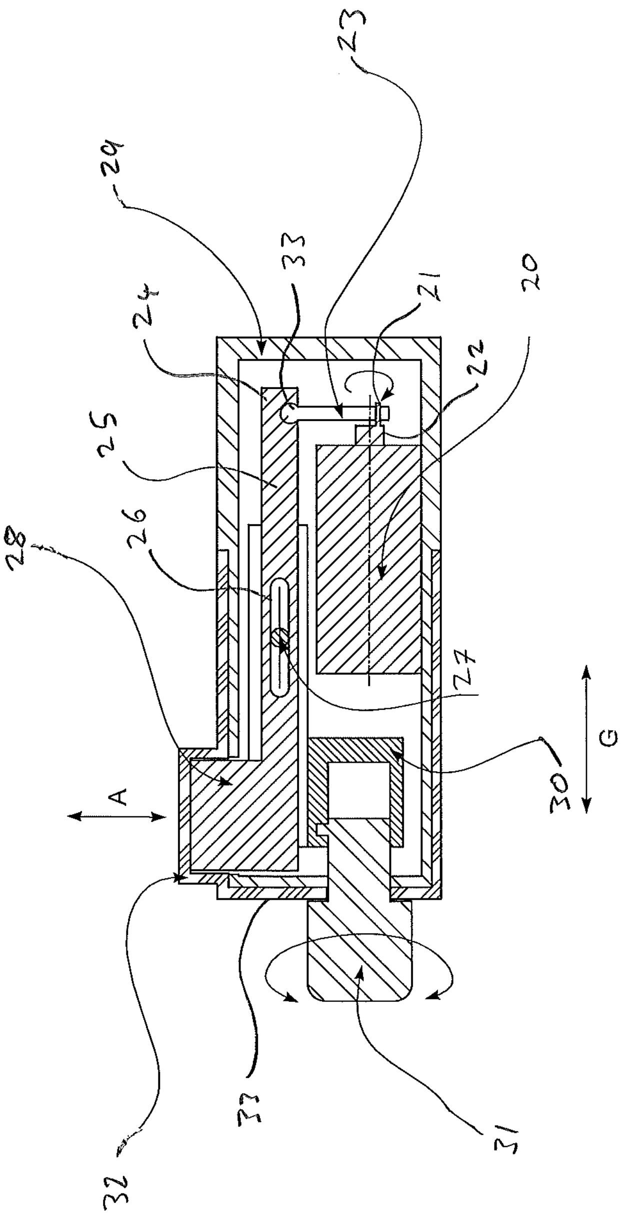
FIG. 3 is a section through a device in accordance with the invention. In an embodiment, the device shown in this figure can be housed within a casing as illustrated in FIG. 2. The drawing is not to scale.

The device shown in FIG. 3 can be employed without an additional housing, or it can be housed inside the vibratory part 10 of the device shown in FIG. 2 and arranged to provide vibrations to the vibratory surface 1.

The device shown in FIG. 3 comprises an electric motor 20 with a drive pin 21 eccentrically mounted on its output shaft 22. The drive pin 21 engages a connecting rod 23, which extends between the pin 21 and a first end portion 24 of a rocking beam 25, to drive the connecting rod 23 in lengthwise reciprocation in response to rotation of the motor's output shaft 22. The rocking beam 25 has a lengthwise extending slot 26 midway between its coupling with the connecting rod 23, embodied by a ball joint 33, and a pad 28, located at the other end of the rocking beam 25. A pivot pin 27 extends through the slot 26, and the rocking beam 25 is arranged to "see-saw" about the pivot pin 27 in response to lengthwise reciprocation of the connecting rod 23. The pad 28 is located within the device casing 29 such that its reciprocation, caused by the see-sawing of the rocking beam 25, is transmitted to the user, via a compliant sleeve portion 32 of the casing 29, as vibrations in the direction shown by arrow A. The pivot pin 27 is mounted so that its location along the slot 26 can be adjusted, relative to the rocking beam 25. Movement of the pivot pin 27 along the slot 26, in the direction of arrow G, changes the relative separation of the connecting rod 23, pivot pin 27 and pad 28 and thus provides a means for adjusting the amplitude of the vibrations the pad 28 imparts to the user. The pivot pin 27 is fixed in a carrier 30 that is slidably mounted and held in place within the casing 29 by an adjustment knob 31. The adjustment knob 31 extends through and is in screw threaded engagement with an end wall 33 of the casing 29. Turning the adjustment knob 31 causes it to screw into or out of the casing 29 and thereby move the carrier 30 and pivot pin 27 along the slot 26 and relative to the rocking beam 25. The frequency of the vibrations imparted by the pad 28 can be adjusted by increasing or decreasing the rotational speed of the motor 20. This is done via a remote control (not shown) that is connected to the motor 20 via a cable (not shown). The cable also provides a power supply to the motor from a battery located in the remote control.

When the device shown in FIG. 3 is housed inside the vibratory part 10 of the device shown in FIG. 2, the adjustment knob 12 of the latter engages with the adjustment knob 31, such that turning the adjustment knob 12 causes the adjustment knob 31 to turn and screw into or out of the casing 29 and thereby adjust the position of the pivot pin 27. The casing 29 should be located within the vibratory part 10 such that the pad 28 is immediately underneath the vibratory surface 1, with the compliant sleeve portion 32 of the casing 29 in contact with the underside of the vibratory surface 1, so as to ensure a good, vibration transmitting, coupling between the pad and the vibratory surface 1.

The invention claimed is:

1. A device for stimulating the frenulum of the male genitalia comprising:

vibratory means configured to be positioned against and apply vibrations to the frenulum;

control means configured to control and/or adjust the amplitude and frequency of the vibrations applied to the frenulum; and an attachment means configured to hold the vibratory part in place against the frenulum, wherein the vibratory means comprises a rocking beam pivotally mounted on a pivot and driven to reciprocally rock in a see-saw motion about the pivot wherein the pivot is mounted such that its axis of engagement with the rocking beam can be adjusted lengthwise along the rocking beam by the control means so as to adjust the amplitude of the vibrations applied to the frenulum.

2. A device as claimed in claim 1, wherein the vibratory part comprises a vibratory surface which is configured to be positioned against the frenulum wherein the vibratory surface is concave.

3. A device as claimed in claim 2, wherein the vibratory surface is made from a malleable material which transmits vibrations and whose shape can be moulded.

4. A device as claimed in claim 1, wherein the pivot comprises a pin, and the pin extends into a slot formed lengthwise in the rocking beam and is mounted so that its location along the slot can be adjusted wherein the pivot pin is fixed in a carrier that is slidably mounted within the vibratory part of the device and held in place by an adjustment knob fixed in screw threaded engagement with the vibratory part, the arrangement being such that turning the adjustment knob causes it to screw into or out of the vibratory part and thereby move the carrier and pivot pin along the slot and relative to the rocking beam.

5. A device as claimed in claim 1, wherein the rocking beam is driven by a connecting rod, itself driven by an eccentric drive pin on located on a rotatable drive shaft.

6. A device as claimed in claim 1, wherein the frequency of the vibrations is up to 150 Hz.

7. A device as claimed in claim 1, wherein the amplitude of the vibrations is preferably up to 3 mm.

8. A device as claimed in claim 1, wherein the control means are separate from the vibratory part.

9. A device as claimed in claim 1, wherein the control means comprises an adjustment knob configured to control at least one of the frequency and amplitude of the vibrations.

10. A device as claimed in claim 1, wherein the device is battery operated and battery is located within a housing which is separate from the vibratory part.

* * * * *